United States Patent
Kazakov et al.

(10) Patent No.: US 9,809,847 B2
(45) Date of Patent: Nov. 7, 2017

(54) METHODS AND COMPOSITIONS FOR DETECTING POLYNUCLEOTIDES AND FRAGMENTS THEREOF

(71) Applicant: SomaGenics, Inc., Santa Cruz, CA (US)

(72) Inventors: Sergei A. Kazakov, San Jose, CA (US); Catharina Casper-Lindley, Santa Cruz, CA (US); Anne Dallas, Santa Cruz, CA (US); Heini Ilves, Santa Cruz, CA (US); Brian H. Johnston, Scotts Valley, CA (US)

(73) Assignee: SOMAGENICS, INC., Santa Cruz, CA (US)

( * ) Notice: Subject to any disclaimer, the term of this patent is extended or adjusted under 35 U.S.C. 154(b) by 0 days.

(21) Appl. No.: 15/318,640

(22) PCT Filed: Jun. 19, 2015

(86) PCT No.: PCT/US2015/036761
§ 371 (c)(1),
(2) Date: Dec. 13, 2016

(87) PCT Pub. No.: WO2015/196120
PCT Pub. Date: Dec. 23, 2015

(65) Prior Publication Data
US 2017/0121762 A1    May 4, 2017

Related U.S. Application Data

(60) Provisional application No. 62/014,569, filed on Jun. 19, 2014.

(51) Int. Cl.
*C12Q 1/68*      (2006.01)
(52) U.S. Cl.
CPC .................... *C12Q 1/6851* (2013.01)
(58) Field of Classification Search
None
See application file for complete search history.

(56) References Cited

U.S. PATENT DOCUMENTS

| | | |
|---|---|---|
| 2004/0115674 A1 | 6/2004 | Knott et al. |
| 2005/0250147 A1* | 11/2005 | Macevicz ............ C12Q 1/6809 435/6.12 |
| 2010/0279305 A1 | 11/2010 | Kuersten |
| 2012/0164651 A1 | 6/2012 | Kazakov et al. |
| 2013/0189684 A1 | 7/2013 | Ehrich et al. |

OTHER PUBLICATIONS

Schmittgen et al, Real-time PCR quantification of precursor and mature microRNA, Methods. Jan. 2008; 44(1): 31-38.*

Kumar et al., miR-ID: a novel, circularization-based platform for detection of microRNAs, RNA. Feb. 2011;17(2):365-80. doi: 10.1261/rna.2490111. Epub Dec. 17, 2010.*
Oberli, Andrea et al., Expression profiling with RNA from formalin-fixed, paraffin-embedded material, Apr. 19, 2008, vol. 1, Issue No. 9.
Desai, Neelam et al., Single-strand-specific nucleases, FEMS Microbiology Reviews 26:457-491 (2003).
Shagin, Dmitry A. et al., A Novel Method for SNP Detection Using a New Duplex-Specific Nuclease From Crab Hepatopancreas, 2002, vol. 12, 1935-1942.
Espinosa, Enrique et al., Comparison of Prognostic Gene Profiles Using qRT-PCR in Paraffin Samples: A Retrospective Study in Patients with Early Breast Cancer, Jun. 15, 2009 , vol. 4, Issue No. 6, e5911.
Wang, G. et al., DNA amplification method tolerant to sample degradation, 2004, vol. 14, 2357-2366.
International Application No. PCT/US2015/036761 International Preliminary Report on Patentability dated Dec. 20, 2016.
International Application No. PCT/US2015/36761 Search Report and Written Opinion dated Oct. 13, 2015.
Iwamoto, Takayuki et al., Predicting prognosis of breast cancer with gene signatures: are we lost in a sea of data? Genome Med 2(11):81 (2010).
Antonov, Janine et al., Reliable gene expression measurements from degraded RNA by quantitative real-time PCR depend on short amplicons and a proper normalization, Jun. 13, 2005, vol. 85, 1040-1050.
Koch; I. et al., Real-time quantitative RT-PCR shows variable, assay-dependent sensitivity to formalin fixation: implications for direct comparison of transcript levels in paraffin-embedded tissues, Sep. 15, 2006, vol. 15, Issue No. 3, 149-156.
Ravo, Maria et al., Quantitative expression profiling of highly degraded RNA from formalin-fixed, paraffin-embedded breast tumor biopsies by oligonucleotide microarrays, 2008, vol. 88, 430-440.
Stump, Mark et al., The use of modified primers to eliminate cycle sequencing artifacts, 1999, vol. 27, Issue 23, 4642-4648.
Maunders, M.J. Polynucleotide Kinase (EC 2.7.1.78), Methods in Molecular Biology 16:343-356 (1993).
Cronin, Maureen et al., Measurement of Gene Expression in Archival Paraffin-Embedded Tissues, Jan. 2004, vol. 164, No. 1, 35-42.
Pinzani, Pamela et al., Circulating nucleic acids in cancer and pregnancy, Apr. 2010, vol. 50, Issue No. 4, 302-307.
Kumar, Pavan et al., miR-ID: A novel, circularization-based platform for detection of microRNAs, 2011, vol. 17, 365-380.

(Continued)

*Primary Examiner* — Aaron Priest
(74) *Attorney, Agent, or Firm* — Wilson Sonsini Goodrich & Rosati

(57) ABSTRACT

Disclosed herein are compositions and methods for the processing, amplification and detection of polynucleotides using target-specific oligonucleotides (TSOs). Hybridization of TSOs to target polynucleotides guides target processing into and purification of small target fragments that then can be amplified and detected with high sensitivity and reproducibility. The method is specifically beneficial for highly degraded polynucleotides found in biological samples.

21 Claims, 8 Drawing Sheets

(56) References Cited

OTHER PUBLICATIONS

Theophile; K., Amplification of mRNA from laser-microdissected single or clustered cells in formalin-fixed and paraffin-embedded tissues for application in quantitative real-time PCR, Jun. 2008, vol. 17, Issue 2 , 101-106.

Lindahl, Tomas. Instability and decay of the primary structure of DNA, Apr. 22, 1993, vol. 362, 709-715.

Huang, Z. et al., Selective labeling and detection of specific mRNA in a total-RNA sample, Nov. 15, 2003, vol. 322, Issue No. 269-274.

* cited by examiner

| Sample | ΔCt (Ct$_{HER2}$- Ct$_{GAPDH}$) | ΔΔCt | $2^{ΔΔCt}$ |
|---|---|---|---|
| B1 (−) | −2.99 | 0 | 1 |
| B3 (−) | −3.05 | −0.06 | 1.04 |
| B2 (+) | −4.93 | −1.94 | 3.84 |
| B4 (+) | −6.63 | −3.63 | 12.42 |

METHODS AND COMPOSITIONS FOR DETECTING POLYNUCLEOTIDES AND FRAGMENTS THEREOF

CROSS-REFERENCE

This application is a U.S. National Stage entry of International Application No. PCT/US15/36761, filed Jun. 19, 2015, which claims the benefit of U.S. Provisional Application No. 62/014,569, filed Jun. 19, 2014, which is incorporated by reference herein in its entirety.

GOVERNMENT SUPPORT

This invention was made with government support under Small Business Innovation Research grant 1R43CA159743-01A1 awarded by the National Institute of Health. The US government has certain rights in the invention.

FIELD OF THE INVENTION

The present invention is in the field of molecular diagnostics. More specifically, it concerns methods and compositions useful for identification, detection, quantification, expression profiling of fragmented RNAs and other polynucleotides isolated from biological samples. The present invention finds use in a variety of genomic research and diagnostic applications, in fields including clinical and forensic research. The RNA(s) of interest may represent biomarker(s) correlating to specific types of cancer or other diseases such as genetic and metabolic disorders, and viral or bacterial infections. They may also represent indicators of response to specific types of therapy.

BACKGROUND OF THE INVENTION

Cancer is a heterogeneous disease characterized by divergent biological and clinical behaviors with different outcomes in different patients in apparently similar pathologic settings (Iwamoto, T., Pusztai, L. 2010. *Genome Med.* 2: 81). Subtle differences in the gene expression and processing of RNA molecules by otherwise undistinguishable tumors can underscore substantial differences in the prognostic outcome, in particular its recurrence and responsiveness to therapy (Ravo, M. et al. 2008. *Lab. Invest.* 88: 430-40).

RNA expression profiling may be very useful for the discovery and validation of biomarkers for cancer (as well as for other diseases), for tumor classification, for understanding the mechanisms of disease progression, for optimizing treatment for individual patients (e.g., identification of companion diagnostics) and for assessing progress during treatment).

SUMMARY OF THE INVENTION

Disclosed herein are target-specific oligonucleotides that are complementary to at least a portion of a target polynucleotide comprising: a first TSO region that hybridizes to a first target polynucleotide region; a second TSO region that hybridizes to a second target polynucleotide region; a third TSO region that hybridizes to a third target polynucleotide region; and a modification that prevents the TSO from: acting as a template and/or as a primer for DNA polymerase; and circularizing; wherein the second TSO region connects the first and third TSO regions; and wherein upon hybridization of the TSO to the target polynucleotide, the first and third target polynucleotide regions become substrates for cleavage by a cleaving agent, and the second region of the target polynucleotide is not a substrate to cleavage by the cleaving agent, allowing for the generation of a processed TSO-hybridized polynucleotide comprising: the TSO; and a processed target polynucleotide comprising the second target polynucleotide region. The first and third TSO regions may be DNA, the second TSO region may be RNA and the target polynucleotide is RNA. The cleaving agent may be ribonuclease H or analog thereof. The modification may be selected from a 2'-$NH_2$, 2'-NHR, a 2'-OMe, 2'-O-alkyl, 2'-F, and 2'-halo; an abasic moiety, a non-nucleotide moiety, a 2',3'-cyclic phosphate, 2'-p/3'-p; 3'-$NH_2$, 3'-NHR, a 3'-biotin moiety, a 3'-digoxigenin moiety, a 3'-dideoxynucleotide, and a 3'-inverted nucleotide; 5'-O-Me, 5'-$NH_2$, 5'-NHR, a 5'-biotin moiety, and 3'-digoxigenin moiety.

Further disclosed herein are methods for detecting a target polynucleotide, comprising: hybridizing the target polynucleotide with a target specific oligonucleotide (TSO) to produce a TSO-hybridized target polynucleotide, wherein the TSO comprises: a first TSO region that hybridizes to a first target polynucleotide region; a second TSO region that hybridizes to a second target polynucleotide region; and a third TSO region that hybridizes to a third target polynucleotide region; wherein the second TSO region connects the first and third TSO regions; and wherein upon hybridization of the TSO to the target polynucleotide, the first and third of target polynucleotide regions become substrates for cleavage by a cleaving agent, and the second target polynucleotide region is not a substrate to cleavage by the cleaving agent; cleaving the target polynucleotide at a first site within the first target polynucleotide region and a second site within the third target polynucleotide region to generate a TSO-hybridized processed polynucleotide comprising: a processed target polynucleotide comprising the second target polynucleotide region; and the TSO, wherein the processed target polynucleotide is hybridized to the TSO; and amplifying the processed target polynucleotide to produce an amplified processed polynucleotide. The method may further comprise purifying or isolating the TSO-hybridized processed polynucleotide. The purifying or isolating the TSO-hybridized processed polynucleotide may comprise: capturing the TSO-hybridized processed polynucleotide to produce a captured TSO-hybridized processed polynucleotide; and separating the captured TSO-hybridized processed polynucleotide from other polynucleotides or their fragments and other solutes that are not hybridized to the TSO. The TSO may comprise a capture moiety and wherein capturing the TSO-hybridized processed polynucleotide comprises capturing the capture moiety with a binding moiety. The processed target polynucleotide may be at least partially hybridized to the TSO while amplifying. The method may further comprise releasing the processed target polynucleotide from hybridization with the TSO before amplifying. The method may further comprise detecting the amplified processed polynucleotide. Amplifying the processed target polynucleotide may comprise circularizing the processed target polynucleotide to produce a circular processed polynucleotide. The circularizing may occur without complete dissociation of the processed target polynucleotide from the TSO. The circularizing may occur with at least partial dissociation of the processed target polynucleotide from the TSO. The circularizing may comprise contacting the processed target polynucleotide with a ligase. The ligase may be a thermostable ligase. The thermostable ligase may be selected from: CircLigase ssDNA Ligase™, CircLigase II™, or CircLigase RNA Ligase™, and Thermostable RNA Ligase™. The method may further comprise enriching the circular processed polynucleotide by cleaving a non-circularized processed polynucleotide with an exonuclease. The method may further comprise detecting the circular processed polynucleotide. The detecting may comprise sequencing the circular processed polynucleotide. The sequencing may comprise a method selected from a group consisting of: Sanger sequencing, next-generation sequencing and direct single-molecule sequencing. The detecting may comprise an amplification method selected from a group consisting of: rolling circle amplification (RCA), hyperbranched RCA, RT-RCA, PCR and its variants, digital PCR, qPCR, and RT-qPCR. The RT-qPCR may be miR-ID® or a variation thereof. The target polynucleotide may be RNA. The target polynucleotide may be DNA. The processed target polynucleotide may be in the range of 13 to 100 nucleotides. The processed target polynucleotide may be in the range of 18 to 60 nucleotides. The processed target polynucleotide may be in the range of 20 to 30 nucleotides. The second TSO region may possess a sequence that contains one or more mismatches with a sequence of the second target polynucleotide region. The first and third TSO regions may consist essentially of DNA and the second TSO region consists essentially of RNA. The first and/or third TSO region may comprise a chemically modified deoxyribonucleotide. The second TSO region may comprise a chemically modified ribonucleotide. The cleaving may be accomplished by ribonuclease H or analog thereof. The second TSO region may comprise a nucleotide mismatched to the second target polynucleotide region. The second TSO region may comprise a nucleotide mismatched to the second target polynucleotide region at a frequency of at least about 1 in 8 nucleotides. The cleaving of the TSO-hybridized DNA polynucleotide may be performed by a duplex-specific nuclease. The first and/or third TSO regions may further comprise a catalytic nucleic acid moiety that cleaves the target polynucleotide after hybridization with the TSO, wherein the catalytic nucleic acid moiety is located in a region of the first and/or third TSO regions having a non-complementary sequence to the target polynucleotide. The capture moiety may be selected from the group consisting of: a hapten, a ligand, a metal-chelating moiety, a nanoparticle, and a linker. The hapten may be biotin and the binding moiety may comprise streptavidin. The hapten may be digoxigenin and the binding moiety may comprise an anti-digoxigenin antibody, or fragment thereof. The binding moiety may be located on a solid support. The solid support may be selected from a group consisting of: magnetic beads, non-magnetic beads, membranes, filters, slides, chips, microtiter plates, and microcapillaries. The TSO may be attached to a solid support. The TSO may be covalently attached to the solid support. The TSO may be non-covalently attached to the solid support. The target polynucleotide may be obtained from a sample selected from the group consisting of: a sample that contains partially degraded polynucleotides; a formaldehyde-fixed paraffin-embedded (FFPE) tissue block; a cell lysate; a serum sample; a plasma sample; and a cell-free bio fluid. The target polynucleotide may be present in a sample selected from the group consisting of: a sample that contains partially degraded polynucleotides; a formaldehyde-fixed paraffin-embedded (FFPE) tissue block; a cell lysate; a serum sample; a plasma sample; and a cell-free bio fluid. The target polynucleotide may be detected directly in the sample without prior isolation and/or purification of total RNA and/or DNA in the sample. The target polynucleotide may comprise an RNA selected from a group consisting of: mRNA, viral RNA, viroid and virusoid RNA, ribosomal RNA, tRNA, pre-tRNA, lncRNA, snRNA, pre-miRNA, pri-miRNA, circular RNA (circRNA), vector-expressed RNA, RNA transcripts, synthetic RNA. The target polynucleotide may comprise a DNA selected from a group consisting of: genomic DNA, viral DNA, mitochondrial DNA, amplified DNA, plasmid DNA, synthetic DNA.

Disclosed herein are kits for detecting a target polynucleotides, comprising a target-specific oligonucleotide (TSO) disclosed herein and one or more of the following components: a hybridization buffer; a cleavage buffer; an enrichment/wash buffer; a release buffer; a circularization buffer; one or more target-specific RT primers; and one or more target-specific PCR primers. The hybridization buffer may be used for hybridizing the target polynucleotide and the TSO. The cleavage buffer may be used for cleaving the first and third target polynucleotide regions. The enrichment/wash buffer may be used for separating of the processed TSO-hybridized target sequence from non-hybridized polynucleotides and/or non-processed polynucleotides. The release and circularization buffers may be a single release-and-circularization buffer. The single release-and-circularization buffer may be used for: dissociating the processed target polynucleotide from the TSO to produce a released processed target polynucleotide; and circularization of the released processed target polynucleotide. The one or more target-specific RT primers may be used for reverse transcription-rolling circle amplification (RT-RCA) of the processed target polynucleotide. The one or more target-specific PCR primers may be used for PCR amplification of a product of the RT-RCA. The kit may comprise two or more target-specific PCR primers.

DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 1A: Comparison of the required mRNA length for standard probe-based (black line) and for mR-FQ methods (black line and all grey lines) for detection of fragmented mRNAs. FIG. 1B: mR-FQ steps: TSOs are employed to capture target mRNA fragments from total RNA that has been isolated from FFPE samples or other sources. TSOs direct/guide the processing of mRNA fragments into uniform lengths and sequences by RNAse H, which cleaves RNA only in DNA-RNA duplexes. Excised, TSO-hybridized mRNA fragments are captured on magnetic beads, washed and then released back into solution with simultaneous circularization. The RNA circularization prevents its re-hybridization with the TSO. Circularized RNA fragments are quantified by RT-qPCR using the miR-ID® technique.

FIG. 5A shows Bioanalyzer traces of degraded total RNA isolated from breast-cancer (B1 through B8) and prostate cancer (P1 and P2) FFPE tissue samples. FIG. 5B shows Ct values for quantification of HER-2 and GAPDH mRNAs in the FFPE samples by TaqMan assays (left panel) and by mR-FQ (right panel). The dotted line indicates the Ct 37 cut-off value above which data are commonly considered unreliable. The data indicate that mR-FQ assays have significantly higher sensitivity (lower Ct values) and better reproducibility (smaller error bars) than TaqMan assays. FIG. 5C shows delta-delta Ct values calculated from mR-FQ measurements, confirming a higher HER-2/GAPDH ratio in HER-2 positive samples (as determined by immunohistochemistry) than in HER-2 negative samples, validating mR-FQ as a reliable method to measure expression of these genes.

DETAILED DESCRIPTION OF THE INVENTION

Figure 1A:
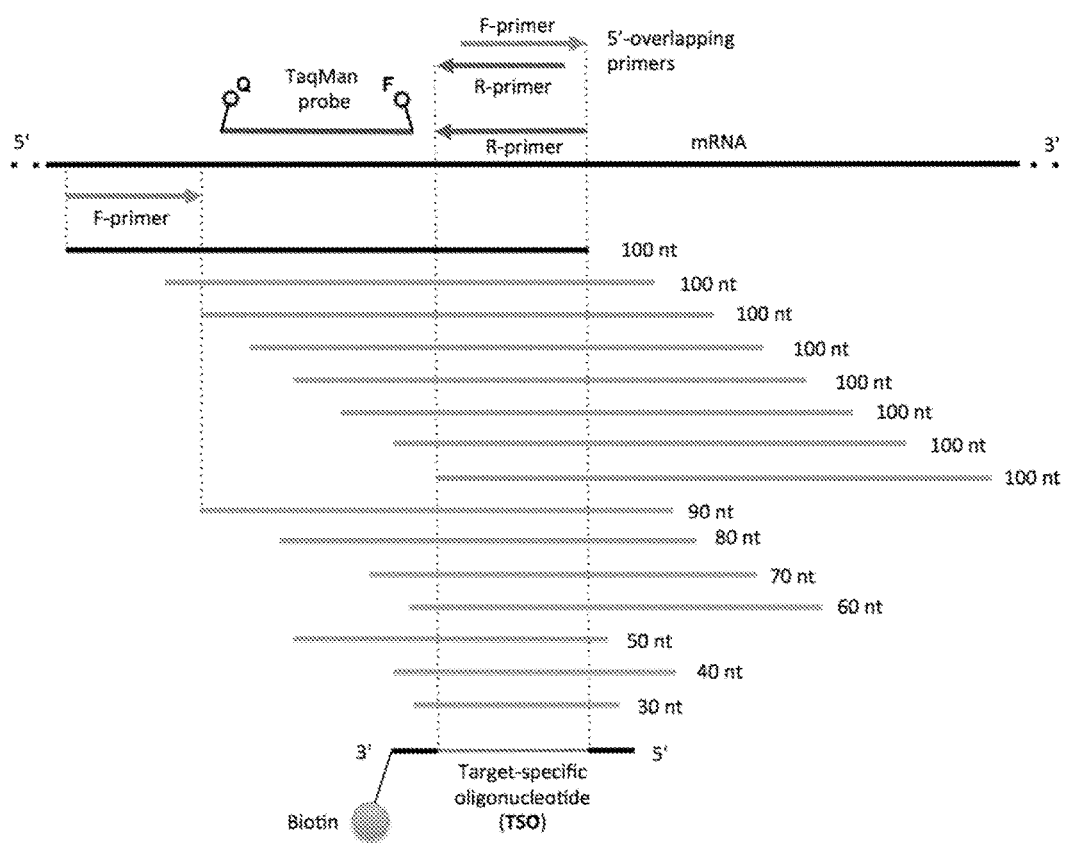
FIG. 1A-B shows a schematic of one embodiment of the mR-FQ approach.

Disclosed herein are target specific oligonucleotides (TSO) and methods for detecting a target polynucleotide in a sample containing a plurality of nucleic acids. The target polynucleotide is generally an RNA molecule (e.g. a messenger RNA or microRNA). The TSO is designed to hybridize to the target polynucleotide. As shown, for example, in FIG. 1B, the TSO has three regions of which two flanking DNA regions make complementary regions of the target polynucleotide a substrate to cleavage by an enzyme upon hybridization of the TSO to the target polynucleotide. The remaining middle RNA region of the TSO protects its corresponding complementary region of the target polynucleotide from cleavage. This regional preferential cleaving is achieved by using a duplex-specific cleaving enzyme that recognizes DNA-RNA hybridized strands, but not RNA-RNA hybridized strands. Therefore, adding the enzyme to a TSO-hybridized target polynucleotide results in processing the TSO-hybridized target polynucleotide into a duplex, the first strand of which comprises the TSO and the second strand of which comprises a region of the target polynucleotide. As described herein, this fragment may be purified, circularized, amplified and detected. These compositions and methods are especially useful for detecting target polynucleotides in samples containing fragmented nucleic acids, such as tissues that have been formalin-fixed and paraffin embedded, which is a common method for preserving biopsy samples.

Various methods disclosed herein are used to detect the resulting fragment of the target polynucleotide. Detection may require reverse transcription and subsequent amplification of the target polynucleotide. Amplification may comprise ligating the ends of the fragment followed by rolling circle amplification.

The compositions and methods disclosed herein are used for analysis of archived tissue such as formalin-fixed paraffin-embedded (FFPE) tissue samples, in conjunction with associated clinical data to identify RNA biomarkers as well as for further understanding of the mechanisms of disease progression. The compositions and methods disclosed herein are not hindered by the chemical modification and fragmentation of RNA molecules that occurs during fixation, histological procedures, and storage, which is largely considered the most common limitation to the detection of the RNA molecules in FFPE samples by RT-qPCR. Due to this fragmentation, only a fraction of the RNA sequences can be amplified. A single cleavage of the RNA anywhere between the primer-specific regions prevents synthesis and amplification of the corresponding cDNA. As a consequence of the fragmentation, the number of RNA molecules available for detection decreases resulting in a decrease in the sensitivity of RT-qPCR assays. The present invention addresses these limitations.

Before the present methods and compositions are described, it is to be understood that this invention is not limited to any particular method or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

It must also be noted that as used herein and in the appended claims, the terms "hybridize" and "bind" are used interchangeably, unless otherwise specified. The terms "hybridize" and "bind" may include, but are not limited to, forming a duplex between complementary nucleic acid strands via Watson-Crick (WC) base pairing. The terms "hybridize" and "bind" may include, but are not limited to, non-WC base-pairing, triplex or tetraplex formation, base-stacking and intercalations; as well as binding with ribozyme moieties, of which catalytic centers may interact with a cleavage site of target polynucleotide via complicated H-bonds, water, metal-ion assisted bonds, etc.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Target-Specific Oligonucleotides (TSOs)

Disclosed herein are target-specific oligonucleotides (TSO) that are complementary to at least a portion of a target polynucleotide comprising: a first TSO region that hybridizes to a first target polynucleotide region; a second TSO region that hybridizes to a second target polynucleotide region; and a third TSO region that hybridizes to a third target polynucleotide region; wherein the second TSO region connects the first and third TSO regions; and wherein upon hybridization (or binding) of the TSO to the target polynucleotide, the first and third target polynucleotide regions become substrates for cleavage by a cleaving agent, and the second region of the target polynucleotide is not a substrate to cleavage by the cleaving agent, allowing for the generation of a processed TSO-hybridized target sequence comprising: the TSO; and a processed target polynucleotide comprising the second target polynucleotide region.

Further disclosed herein are target-specific oligonucleotides (TSO) that are complementary to at least a portion of a target polynucleotide comprising: a first TSO region that hybridizes to a first target polynucleotide region; a second TSO region that hybridizes to a second target polynucleotide region; a third TSO region that hybridizes to a third target polynucleotide region; and a modification that prevents the TSO from: (i) acting as a template for DNA polymerase; and (ii) circularizing; wherein the second TSO region connects the first and third TSO regions; and wherein upon hybridization (or binding) of the TSO to the target polynucleotide, the first and third target polynucleotide regions become substrates for cleavage by a cleaving agent, and the second region of the target polynucleotide is not a substrate to cleavage by the cleaving agent, allowing for the generation of a processed TSO-hybridized target sequence comprising: the TSO, and a processed target polynucleotide comprising the second target polynucleotide region.

Upon hybridization (or binding) of the TSO to the target polynucleotide, the resulting TSO-hybridized target polynucleotide may be processed by the cleavage of the target polynucleotide at sites within the first target polynucleotide region and the third target polynucleotide region, generating the processed TSO-hybridized polynucleotide. Upon hybridization (or binding) of the TSO to the target polynucleotide, the resulting TSO-hybridized target polynucleotide may be processed by the cleavage of the target polynucleotide at sites between the second target polynucleotide region and the first/third target polynucleotide regions, generating the processed TSO-hybridized polynucleotide. The TSO-hybridized polynucleotide may be further used as a template for amplification.

One or more nucleotides of the first, second, and/or third TSO regions may be a deoxyribonucleotide. One or more nucleotides of the first, second, and/or third TSO regions may be a ribonucleotide. The deoxyribonucleotide may be chemically modified. The ribonucleotide may be chemically modified.

The first TSO region may comprise DNA. The second TSO region may comprise DNA. The third TSO region may comprise DNA. The first TSO region may comprise RNA. The second TSO region may comprise RNA. The third TSO region may comprise RNA.

The first TSO region may consist essentially of DNA. The second TSO region may consist essentially of DNA. The third TSO region may consist essentially of DNA. The first TSO region may consist essentially of RNA. The second TSO region may consist essentially of RNA. The third TSO region may consist essentially of RNA.

The first TSO region may be DNA, the second TSO region may be RNA, and the third TSO region may be DNA. The first and third TSO regions may comprise DNA nucleotides or modified versions thereof. The second TSO region may comprise RNA nucleotides or modified versions thereof. The TSO may comprise (a) DNA nucleotides in the first and third TSO regions; and (b) RNA and/or 2'-OMe nucleotides in the second TSO region. The first and third TSO regions may consist essentially of DNA and the second TSO region may consist essentially of RNA, wherein one or more of the RNA nucleotides comprises a 2'-OMe modification.

The first TSO region may comprise at least about 1, 2, 3, 4, 5, 6, 7, 8, 9, 10, 11, 12, 13, 14, or 15 nucleotides. The first TSO region may comprise less than about 30, 25, 20, 19, 18, 17, 16, 15, 14, 13, 12, 11 or 10 nucleotides. The first TSO region may comprise between about 3 to about 10 nucleotides. The first TSO region may comprise more than 30 nucleotides.

The second TSO region may comprise at least about 5, about 10, about 15, or about 20 nucleotides. The second TSO region may contain between about 5 to about 40 nucleotides. The second TSO region may contain from about 10 to about 100 nucleotides. The second TSO region may contain about 18 to about 60 nucleotides. The second TSO region may contain about 20 to about 30 nucleotides.

The third TSO region may comprise at least about 1, 2, 3, 4, 5, 6, 7, 8, 9, 10, 11, 12, 13, 14, or 15 nucleotides. The third TSO region may comprise less than about 30, 25, 20, 19, 18, 17, 16, 15, 14, 13, 12, 11 or 10 nucleotides. The third TSO region may comprise between about 3 to about 10 nucleotides. The third TSO region may comprise more than 30 nucleotides.

The first TSO region may be located on a 5' end of the TSO. The first TSO region may be connected to a 5' end of the second TSO region. The third TSO region may be located on a 3' end of the TSO. The third TSO region may be located on a 3' end of the second TSO region.

The first TSO region may be located on a 3' end of the TSO. The first TSO region may be connected to a 3' end of the second TSO region. The third TSO region may be located on a 5' end of the TSO. The third TSO region may be located on a 5' end of the second TSO region.

The TSO may be entirely complementary to the target polynucleotide. The TSO may be entirely complementary to a portion of the target polynucleotide. The TSO may be entirely complementary to a portion of the target polynucleotide, wherein the portion of the target polynucleotide consists of the first, second and third target polynucleotide regions. The first TSO region may be entirely complementary to the first target polynucleotide region. The second TSO region may be entirely complementary to the second target polynucleotide region. The third TSO region may be entirely complementary to the third target polynucleotide region.

The TSO may be partially complementary to the target polynucleotide. The TSO may be partially complementary to a portion of the target polynucleotide. The TSO may be partially complementary to a portion of the target polynucleotide, wherein the portion of the target polynucleotide consists of the first, second and third target polynucleotide regions. The first TSO region may be partially complementary to the first target polynucleotide region. The second TSO region may be partially complementary to the second target polynucleotide region. The third TSO region may be partially complementary to the third target polynucleotide region.

The TSO may comprise a nucleotide mismatch with the target polynucleotide. The TSO may comprise a nucleotide mismatch with the portion of the target polynucleotide to which the TSO hybridize. The first TSO region may comprise a nucleotide mismatch with the first target polynucleotide region. The second TSO region may comprise a nucleotide mismatch with the second target polynucleotide region. The third TSO region may comprise a nucleotide mismatch with the third target polynucleotide region.

The TSO may comprise more than one nucleotide mismatch with the target polynucleotide. The TSO may comprise more than one nucleotide mismatch with the portion of the target polynucleotide to which the TSO hybridize. The first TSO region may comprise more than one nucleotide mismatch with the first target polynucleotide region. The second TSO region may comprise more than one nucleotide mismatch with the second target polynucleotide region. The third TSO region may comprise more than one nucleotide mismatch with the third target polynucleotide region. The number of nucleotide mismatches may be 1, 2, 3 or more. The number of mismatches may be 8, 7, 6, 5, 4 or fewer. The nucleotide mismatches between the TSO and target polynucleotide or their respective regions may occur with a frequency of about 1 in 4, about 1 in 5, about 1 in 6, about 1 in 7, about 1 in 8, about 1 in 9, about 1 in 10, about 1 in 15, about 1 in 20, about 1 in 25, about 1 in 30, about 1 in 35, about 1 in 40, about 1 in 45, about 1 in 50, about 1 in 55, about 1 in 60, about 1 in 70, about 1 in 80, about 1 in 90 or about 1 in 100.

Chemical Modifications

The TSO may comprise one or more modifications. One or more nucleotides of the first, second, and/or third TSO regions may comprise one or more chemical modifications. The one or more chemical modifications may comprise an alkyl group or a halo group. The one or more chemical modifications may be selected from 2'-OMe, 2'-O-alkyl, 2'-F, 2'-halo, and 2'-$NH_2$. The one or more modifications may also comprise one or more abasic sites or non-nucleotide linkers such as described in U.S. Pat. No. 7,205,129.

At least about 1%, 3%, 5%, 10%, 15%, or 20% of the nucleotides of the first, second, and/or third TSO regions may comprise one or more chemical modifications. Less than about 90%, 80%, 70%, 60%, 50%, or 40% of the nucleotides of the second TSO region may comprise one or more chemical modifications.

The one or more chemical modifications may prevent the TSO from acting as a template and/or as a primer for DNA polymerase. The one or more chemical modifications may prevent the TSO from circularizing. The one or more chemical modifications may be selected from a 2'-$NH_2$, 2'-NHR, a 2'-OMe, 2'-O-alkyl, 2'-F, and 2'-halo; an abasic moiety, a non-nucleotide moiety, a 2',3'-cyclic phosphate, 2'-p/3'-p,3'-p; 3'-$NH_2$, 3'-NHR, a 3'-biotin moiety, a 3'-digoxigenin moiety, a 3'-dideoxynucleotide, and a 3'-inverted nucleotide; 5'-OMe, 5'-OR, 5'-$NH_2$, 5'-NHR, a 5'-biotin moiety, and 3'-digoxigenin moiety, wherein R is selected from an alkyl, a non-nucleotide linker, a chemical group, a happen, a ligand, a reactive chemical group, a reactive photochemical group, a chelating moiety, a hydrophobic moiety, an intercalating moiety, a positively or negatively charged moiety, a minor grove binder, a major groove binder, a nucleic acid moiety or modified variants thereof, an amino acid moiety or modified variants thereof, a lipid moiety or modified variants thereof, and a hydrocarbon moiety or modified variants thereof.

In some embodiments of the inventions, one or more nucleotides of TSO may comprise chemical modifications that prevent one or more biochemical reactions selected from the list: (a) extension of its 3'-end by a polymerase; (b) its serving as a template for a primer extension by a polymerase; (c) ligation of its 5'-end and/or 3'-end by a ligase; and (d) cleavage by nucleases. Chemical modifications that prevent its serving as a template for a primer extension by a polymerase may include one or more residues that cannot be replicated by DNA polymerase, such as abasic site(s) or nucleoside(s) with 2'-OMe or 2'-F modifications.

Capture Moieties

The TSO may comprise a capture moiety. The capture moiety may be conjugated to the TSO. The capture moiety may be conjugated to a 5' end of the TSO. The capture moiety may be conjugated to or located at an internal region of the TSO. The capture moiety may be conjugated to a 3' end of the TSO. The capture moiety may be chemically conjugated to the TSO. The capture moiety may be conjugated to the first TSO region. The capture moiety may be conjugated to a 5' end of the first TSO region. The capture moiety may be conjugated to a 3' end of the first TSO region. The capture moiety may be conjugated to the second TSO region. The capture moiety may be conjugated to a 5' end of the second TSO region. The capture moiety may be conjugated to a 3' end of the second TSO region. The capture moiety may be conjugated to the third TSO region. The capture moiety may be conjugated to a 5' end of the third TSO region. The capture moiety may be conjugated to a 3' end of the third TSO region.

The capture moiety may be bound by a binding moiety. The capture moiety may comprise a moiety selected from the group consisting of a hapten, an antigen, an antibody, a ligand, a receptor, a fluorophore, a metal-chelating moiety, a metal, a nanoparticle, a chemically active group, and a linker. Similarly, the binding moiety may comprise a moiety selected from the group consisting of a hapten, an antigen, an antibody, a ligand, a receptor, a fluorophore, a metal-chelating moiety, a metal, a nanoparticle, a chemically active group, and a linker. The hapten may be biotin or digoxigenin.

The capture moiety may be the antigen and the binding moiety may be the antibody. Alternatively, the capture moiety may be the antibody and the binding moiety may be the antigen. The capture moiety may be the hapten and the binding moiety may be an anti-hapten antibody. Alternatively, the capture moiety may be the anti-hapten antibody and the binding moiety may be the hapten. The capture moiety may be the ligand and the binding moiety may be the receptor. Alternatively, the capture moiety may be the receptor and the binding moiety may be the ligand. The capture moiety may be the metal and the binding moiety may be the metal-chelating moiety. Alternatively, the capture moiety may be the metal-chelating moiety and the binding moiety may be the metal. The capture moiety may comprise biotin and the binding moiety may comprise avidin/streptavidin. Alternatively, the capture moiety may comprise avidin/streptavidin and the binding moiety may comprise biotin. The capture moiety may comprise digoxigenin and the binding moiety may comprise an anti-digoxigenin antibody. Alternatively, the capture moiety may comprise the anti-digoxigenin antibody and the binding moiety may comprise digoxigenin.

The capture moiety may comprise an immobilized oligonucleotide complementary to at least a portion of the TSO. The capture moiety may comprise a thiol group and the binding moiety may comprise a thiol-specific binding moiety that contains a chemically or photo-chemically active group, or vice versa. The capture moiety may comprise an amino group and the binding moiety may comprise an $NH_2$ or —NH-specific binding moiety that contains a chemically or photo-chemically active group.

The binding moiety may be the solid support. The binding moiety may be a component of the solid support. The binding moiety may be attached to the solid support. The binding moiety may coat the solid support.

The TSO may be attached to a solid support before or after hybridization with target polynucleotide. The TSO may be covalently attached to the solid support. The TSO may be non-covalently attached to the solid support.

Methods

Disclosed herein are methods for detecting a target polynucleotide, comprising: hybridizing the target polynucleotide with a target specific oligonucleotide (TSO) to produce a TSO-hybridized target polynucleotide, wherein the TSO comprises: a first TSO region that hybridizes or binds to a first target polynucleotide region; a second TSO region that hybridizes to a second target polynucleotide region; and a third TSO region that hybridizes or binds to a third target polynucleotide region; wherein the second TSO region connects the first and third TSO regions; and wherein upon hybridization of the TSO to the target polynucleotide, the first and third of target polynucleotide regions become a substrate to cleavage by a cleaving agent, and the second region of the target polynucleotide is not a substrate to cleavage by the cleaving agent, allowing for the generation of a processed TSO-hybridized target sequence comprising the TSO hybridized to the second target polynucleotide region; and cleaving the target polynucleotide at a first site within the first target region of the target polynucleotide and a second site within the third target region of the target polynucleotide to generate the processed TSO-hybridized target sequence comprising: (i) a processed polynucleotide comprising the second target polynucleotide region and (ii) the TSO, wherein the TSO is hybridized to the processed target polynucleotide. The processed TSO-hybridized target sequence may comprise a portion of the first TSO region. The processed TSO-hybridized target sequence may comprise a portion of the third TSO region. The portion of the first and/or third TSO region may consist essentially of about 1 nucleotide, about 2 nucleotides, about 3 nucleotides, about 4 nucleotides, about 5 nucleotides, about 6 nucleotides, about 8 nucleotides, about 10 nucleotides, about 12 nucleotides, about 14 nucleotides, about 16 nucleotides, about 18 nucleotides or about 20 nucleotides.

Further disclosed herein are methods for detecting a target polynucleotide, comprising: hybridizing the target polynucleotide with a target specific oligonucleotide (TSO) to produce a TSO-hybridized target polynucleotide, wherein the TSO comprises: a first TSO region that hybridizes to a first target polynucleotide region; a second TSO region that hybridizes to a second target polynucleotide region; a third TSO region that hybridizes to a third target polynucleotide region; and a modification that prevents the TSO from acting as a template for DNA polymerase; wherein the second TSO region connects the first and third TSO regions; and wherein upon hybridization of the TSO to the target polynucleotide, the first and third of target polynucleotide regions become susceptible to cleavage by a cleaving agent, and the second region of the target polynucleotide is comparatively resistant to cleavage by the cleaving agent, allowing for the generation of a processed TSO-hybridized target sequence comprising the TSO hybridized to the second target polynucleotide region; and cleaving the target polynucleotide at a first site within the first target region of the target polynucleotide and a second site within the third target region of the target polynucleotide to generate the processed TSO-hybridized target sequence comprising: (i) a processed polynucleotide comprising the second target polynucleotide region and (ii) the TSO, wherein the TSO is hybridized to the processed target polynucleotide.

Disclosed herein are methods for detecting a target polynucleotide, comprising: hybridizing the target polynucleotide with a target specific oligonucleotide (TSO) to produce a TSO-hybridized target polynucleotide, wherein the TSO comprises: a first TSO region that hybridizes to a first target polynucleotide region; a second TSO region that hybridizes to a second target polynucleotide region; a third TSO region that hybridizes to a third target polynucleotide region; and a modification that prevents the TSO from circularizing; wherein the second TSO region connects the first and third TSO regions; and wherein upon hybridization of the TSO to the target polynucleotide, the first and third of target polynucleotide regions become susceptible to cleavage by a cleaving agent, and the second region of the target polynucleotide is comparatively resistant to cleavage by the cleaving agent; and cleaving the target polynucleotide at a first site within the first target region of the target polynucleotide and a second site within the third target region of the target polynucleotide to generate the processed TSO-hybridized target sequence comprising: (i) a processed polynucleotide comprising the second target polynucleotide region and (ii) the TSO, wherein the TSO is hybridized to the processed target polynucleotide.

Further disclosed herein are methods for detecting a target polynucleotide, comprising: hybridizing the target polynucleotide with a target specific oligonucleotide (TSO) to produce a TSO-hybridized target polynucleotide, wherein the TSO comprises: a first TSO region that hybridizes to a first target polynucleotide region; a second TSO region that hybridizes to a second target polynucleotide region; a third TSO region that hybridizes to a third target polynucleotide region; and a modification that prevents the TSO from (i) acting as a template for DNA polymerase and (ii) circularizing; wherein the second TSO region connects the first and third TSO regions; and wherein upon hybridization of the TSO to the target polynucleotide, the first and third of target polynucleotide regions become susceptible to cleavage by a cleaving agent, and the second region of the target polynucleotide is comparatively resistant to cleavage by the cleaving agent; and cleaving the target polynucleotide at a first site within the first target region of the target polynucleotide and a second site within the third target region of the target polynucleotide to generate the processed TSO-hybridized target sequence comprising: (i) a processed polynucleotide comprising the second target polynucleotide region and (ii) the TSO, wherein the TSO is hybridized to the processed target polynucleotide.

Disclosed herein are methods for detecting a target polynucleotide in a sample, comprising: hybridizing the target polynucleotide present in the sample with a target specific oligonucleotide (TSO) to produce a TSO-hybridized target polynucleotide, wherein the TSO comprises: a first TSO region that hybridizes to a first target polynucleotide region; a second TSO region that hybridizes to a second target polynucleotide region; and a third TSO region that hybridizes to a third target polynucleotide region; wherein the second TSO region connects the first and third TSO regions; and wherein upon hybridization of the TSO to the target polynucleotide, the first and third of target polynucleotide regions become susceptible to cleavage by a cleaving agent, and the second region of the target polynucleotide is comparatively resistant to cleavage by the cleaving agent, allowing for the generation of a processed TSO-hybridized target sequence comprising the TSO hybridized to the second target polynucleotide region; and cleaving the target polynucleotide at a first site within the first target region of the target polynucleotide and a second site within the third target region of the target polynucleotide to generate the processed TSO-hybridized target sequence comprising: (i) a processed polynucleotide comprising the second target polynucleotide region and (ii) the TSO, wherein the TSO is hybridized to the processed target polynucleotide.

Figure 1B:
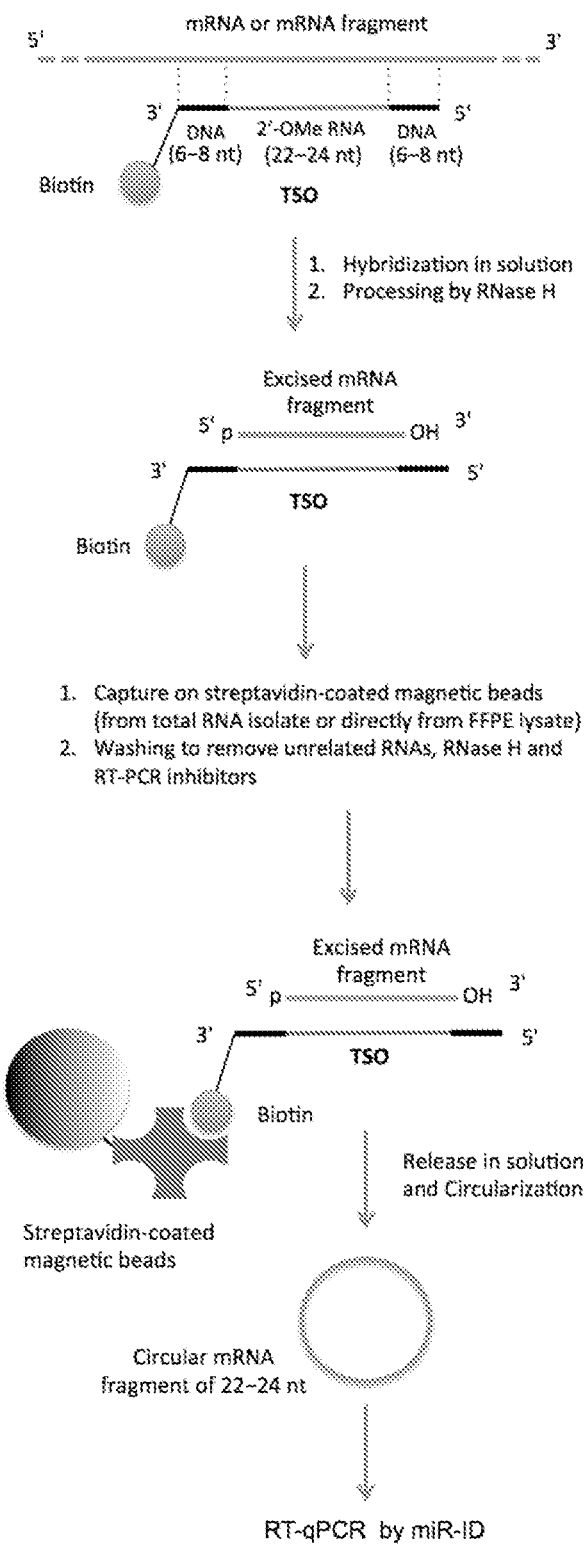

The first and third TSO regions of the TSO may comprise DNA nucleotides, and the second TSO region may comprise 2'-O-methylated (2'-OMe) RNA nucleotides. The first and third TSO regions of the TSO may consist essentially of DNA nucleotides, and the second TSO region may consist essentially of ribonucleotides, wherein one or more ribonucleotides are 2'-O-methylated (2'-OMe) RNA nucleotides. In these instances, the methods may be referred to as mRNA Fragment Quantification (mR-FQ). An exemplary representation of this method is depicted in FIG. 1A-B.

Hybridizing

The methods disclosed herein comprise hybridizing the target polynucleotide with the target specific oligonucleotide. Hybridizing may comprise contacting a sample comprising the target polynucleotide with the TSO to produce the TSO-hybridized target polynucleotides. Contacting the sample may occur in a solution. The sample may be contacted with a solution comprising the TSO. Contacting the sample may occur on a solid phase or support.

The methods may further comprise attaching the TSO to a solid support before hybridizing the target polynucleotide to the TSO. Attaching the TSO to the solid support may comprise covalently attaching the TSO to the solid support. Attaching the TSO to the solid support may comprise non-covalently attaching the TSO to the solid support.

Compositions and methods disclosed herein allow for hybridizing a first TSO and a second TSO to a first target polynucleotide and a second polynucleotide, respectively. For example, the sample may contain a plurality of target polynucleotides and the methods provide for detecting the plurality of target polynucleotides. The first TSO sequence or portion thereof and the second TSO or portion thereof may possess different sequences. The first TSO may comprise a first sequence that is complementary to the first target polynucleotide and the second TSO may comprise a second sequence that is complementary to the second target polynucleotide, wherein the first sequence and the second sequence are different. The first TSO may hybridize to the first target polynucleotide and the second TSO may hybridize to the second target polynucleotide, thereby producing a pool or library of TSO-hybridized target polynucleotides.

The TSO-hybridized target polynucleotide(s) may further be cleaved, amplified, purified, circularized, detected, and/or further manipulated as described herein.

Cleaving

Cleaving the target polynucleotide may comprise use of a cleaving agent. The cleaving agent may be a ribonuclease. The ribonuclease may be selected from the following groups: (a) ribonuclease having a preference for single-stranded RNA over double-stranded RNA (such as RNase A, RNase I, RNase $I_f$, RNase II, or RNase T1, T2, and U2); (b) ribonuclease having a preference for double-stranded RNA over single-stranded RNA (such as RNase V1 or RNase III); and (c) ribonuclease H or analog thereof, which cleaves RNA in DNA-RNA duplexes. The analog may be a mutated version or other enzyme with RNAse H-like activity. Single-strand or double-strand specific nucleases that cleave both DNA and RNA also can be used to cleave the target polynucleotide. Cleaving the target polynucleotide may comprise the use of ribonuclease H.

The cleaving agent may be single-strand specific nuclease or duplex-specific nuclease. The single-strand specific nuclease may be selected from S1, P1, or nucleases from *Alteromonas espejiana* and *Neurospora crassa* (Desai, N. A, Shankar, V. 2003. *FEMS Microbiol. Rev.* 26: 457-91).

In the case of using of a duplex-specific nuclease (Shagin, D. A. et al. 2002. *Genome Res.* 12: 1935-42) that cleaves DNA in both DNA-DNA and RNA-DNA duplexes, the TSO molecules may comprise first and third TSO regions made of DNA nucleotides and the second TSO region made of DNA or RNA (or their derivatives) wherein the second TSO region has at least 1 mismatch for every 8-12 nucleotides in a duplex with a target polynucleotide, wherein the target polynucleotide is a DNA polynucleotide.

The first and/or third TSO region of the TSO may comprise one or more catalytic nucleic acid moieties (such as ribozymes or deoxyribozymes) capable of cleaving the target polynucleotide after its hybridization with the TSO. Thus, the cleaving agent may be a ribozyme or deoxyribozyme. The catalytic nucleic acid moiety may comprise an active center whose sequence is not complementary to the target polynucleotide.

Cleaving the target polynucleotide may occur at a site within the first polynucleotide region. Cleaving the target polynucleotide may occur at a site within the third polynucleotide region. Cleaving the target polynucleotide may occur at a first site within the first polynucleotide region. Cleaving the target polynucleotide at the site within the first/third polynucleotide region may occur when the first/third TSO region is 100% complementary to the first/third target polynucleotide region. Cleaving the target polynucleotide at the site within the first/third polynucleotide region may occur when the first/third TSO region is partially complementary to the first/third target polynucleotide region. Cleaving the target polynucleotide at the site within the first/third polynucleotide region may occur when there are one or more nucleotide mismatches between the first/third TSO region and the first/third target polynucleotide region.

The first/third TSO region may comprise a catalytic nucleic acid moiety. The catalytic nucleic acid moiety may be a ribozyme. The catalytic nucleic acid moiety may be a deoxyribozyme. The catalytic nucleic acid moiety may enable cleavage of the polynucleotide after hybridization with the TSO. The catalytic nucleic acid moiety may comprise an active center with a sequence that is not complementary to the target polynucleotide.

The processed TSO-hybridized polynucleotide may comprise a 5'-phosphate (5'-p) end and/or 3'-hydroxyl (3'-OH) end, or other terminal groups that may be converted into 5'-p and 3'-OH that can be ligated by a RNA ligase in order to circularize the processed target polynucleotide. For example, 5'-OH and 2',3'-cyclic phosphate (or 2'-p/3'-p) ends may be converted using polynucleotide kinase (Maunders, M. J. 1993. *Methods Mol Biol.* 16: 343-56) to 5'-p and 3'-OH ends, respectively.

Purifying

The methods may comprise purifying or isolating the TSO-hybridized processed polynucleotide from a sample or solution (e.g. reaction buffer). Purifying or isolating the TSO-hybridized processed polynucleotide may comprise capturing or binding the TSO-hybridized target polynucleotide or TSO-hybridized processed polynucleotide to produce a captured TSO-hybridized polynucleotide or captured TSO-hybridized processed polynucleotide, respectively. Purifying or isolating the TSO-hybridized (processed) polynucleotide may comprise separating the captured TSO-hybridized (processed) polynucleotide from other polynucleotides that are not hybridized to the TSO, target polynucleotide fragments and/or solutes from the cleaving step. Target polynucleotide fragments may include, but are not limited to, non-target polynucleotides in the sample and fragments of the target polynucleotide as a result of cleaving the target polynucleotide, such as the first target polynucleotide region, the third target polynucleotide region, and fragments thereof.

Capturing/binding the TSO-hybridized (processed) polynucleotide may comprise capturing/binding the TSO-hybridized (processed) polynucleotide on a solid support. The solid support, by way of non-limiting example, may be selected from a magnetic bead, a non-magnetic bead, a nanoparticle, a membrane, a filter, a slide, a chip, a microtiter plate, and a microcapillary.

Capturing/binding the TSO-hybridized (processed) polynucleotide may comprise capturing a capture moiety on the TSO. Capturing/binding the TSO-hybridized (processed) polynucleotide may comprise capturing a capture moiety on the target polynucleotide. The methods may further comprise attaching the capture moiety to the target polynucleotide.

The capture moiety may be bound by a binding moiety. The capture moiety may comprise a moiety selected from the group consisting of a hapten, a hapten-specific aptamer, an antigen, an antibody, a ligand, a receptor, a fluorophore, a metal-chelating moiety, a metal, a nanoparticle, a chemically active group, and a linker. Similarly, the binding moiety may comprise a moiety selected from the group consisting of a hapten, a hapten-specific aptamer, an antigen, an antibody, a ligand, a receptor, a fluorophore, a metal-chelating moiety, a metal, a nanoparticle, a chemically active group, and a linker. The hapten may be biotin or digoxigenin.

The capture moiety may be the antigen and the binding moiety may be the antibody. Alternatively, the capture moiety may be the antibody and the binding moiety may be the antigen. The capture moiety may be the hapten and the binding moiety may be an anti-hapten antibody. Alternatively, the capture moiety may be the anti-hapten antibody and the binding moiety may be the hapten. The capture moiety may be the ligand and the binding moiety may be the receptor. Alternatively, the capture moiety may be the receptor and the binding moiety may be the ligand. The capture moiety may be the metal and the binding moiety may be the metal-chelating moiety. Alternatively, the capture moiety may be the metal-chelating moiety and the binding moiety may be the metal. The capture moiety may comprise biotin and the binding moiety may comprise avidin/streptavidin. Alternatively, the capture moiety may comprise avidin/streptavidin and the binding moiety may comprise biotin. The capture moiety may comprise digoxigenin and the binding moiety may comprise an anti-digoxigenin antibody. Alternatively, the capture moiety may comprise the anti-digoxigenin antibody and the binding moiety may comprise digoxigenin.

The binding moiety may be the solid support. The binding moiety may be a component of the solid support. The binding moiety may be attached to the solid support. The binding moiety may coat the solid support.

The methods may further comprise separating the captured TSO-hybridized polynucleotide and/or TSO-hybridized processed polynucleotide from one or more molecules, fragments, or solutes in the sample. The separating may comprise washing the captured TSO-hybridized (processed) polynucleotide. Washing may occur under conditions that do not disassociate the TSO from the processed target polynucleotide. The separating may comprise running the captured TSO-hybridized (processed) polynucleotide on a gel (e.g. gel electrophoresis).

Circularizing

The methods may further comprise circularizing the TSO-hybridized processed polynucleotide to produce a circular processed polynucleotide. The methods may further comprise circularizing the processed polynucleotide to produce a circular processed polynucleotide. Circularizing the TSO-hybridized processed polynucleotide may comprise ligating the ends of the TSO-hybridized processed polynucleotide. Circularizing the processed target polynucleotide may comprise ligating the ends of the processed target polynucleotide. Circularizing the processed target polynucleotide may comprise intramolecularly ligating the ends of the processed target polynucleotide.

The TSO-hybridized processed polynucleotide may be dissociated before circularizing to separate the processed target polynucleotide and the TSO of the TSO-hybridized processed polynucleotide. Disassociating and circularizing may occur simultaneously. Disassociating and circularizing may occur sequentially. The TSO-hybridized processed polynucleotide may be partially dissociated before circularizing to separate the processed target polynucleotide and the TSO. The partial dissociation may be performed by applying one or more of following conditions: elevated temperature, adding denaturing agent (such as DMSO, urea or formamide), adding a buffer with low or high pH. The TSO-hybridized processed polynucleotide may be about 5%, about 10%, about 15%, about 20%, about 25%, about 30%, about 40%, about 50%, about 60%, about 70%, about 80%, about 90% or about 90% dissociated, before circularizing to separate the processed target polynucleotide and the TSO. The method may comprise circularizing the processed target polynucleotide when it is partially disassociated from the TSO. The method may comprise circularizing the processed target polynucleotide when it is entirely disassociated from the TSO.

Circularizing the processed target polynucleotide may comprise ligating the ends of the processed target polynucleotide to produce a circularized processed polynucleotide. Ligating may comprise use of one or more enzymes. The one or more enzymes may be a ligase. The ligase may be selected from a group of ligases comprising: T4 RNA ligase 1, T4 RNA ligase 2 or its derivatives, and human recombinant RtcB ligase. The ligase may be thermostable ligase. The thermostable ligase may be selected from a CircLigase ssDNA ligase, CircLigase II, CircLigase RNA ligase or Thermostable RNA ligase.

The benefits of circularizing the processed target polynucleotide may include: (a) reduced ability to re-hybridize with the TSO, which may increase the amount available for a subsequent amplification reaction; (b) an ability of the circularized fragments to be amplified by rolling-circle amplification (RCA) or to be pre-amplified by RCA before amplification by PCR; and (c) reducing the amount of non-target-specific amplification by eliminating non-circular nucleic acids that may serve as primers or templates.

The circularized processed target polynucleotides may be enriched by cleaving non-circularized molecules. Cleaving the non-circularized molecules may comprise use of one or more exonucleases. The exonucleases may be selected from the group comprising Exonuclease I, Exonuclease III, Exonuclease VII, T5 Exonuclease, Terminator™ 5'-Phosphate-Dependent Exonuclease, RecJ$_f$, Rec J exonuclease, and RNAse R.

The TSO-hybridized polynucleotide(s) or the TSO-hybridized polynucleotide fragment(s) may be (a) captured on a solid support to produce captured polynucleotide fragments; and (b) separated from other polynucleotides or their fragments and other solutes that may be not hybridized to TSO(s) prior to the release and/or circularization of the TSO-hybridized, processed polynucleotide fragment(s).

Amplifying

The methods may further comprise amplifying the processed target polynucleotide to produce an amplified processed polynucleotide. The method may further comprise the amplifying the processed target polynucleotide to produce a plurality of processed polynucleotides. The plurality of processed polynucleotides may be a plurality of individual copies of the processed target polynucleotide. The plurality of processed polynucleotides may be a multimer or concatamer of the processed target polynucleotide.

Amplifying may be performed before dissociation of the processed target polynucleotide from the TSO. Amplifying may be performed after dissociation of the processed target polynucleotide from the TSO. Amplifying may be performed after partial dissociation of the processed target polynucleotide from the TSO. Amplifying and dissociation of the processed target polynucleotide from the TSO may occur simultaneously. Amplifying may occur before circularizing. Circularizing may occur before amplifying. Amplifying, circularizing, and dissociation of the processed target polynucleotide from the TSO may occur simultaneously. The methods may further comprise the amplifying and/or detecting of the processed TSO-hybridized target polynucleotide performed without dissociation from the TSO.

Amplifying the processed polynucleotide may comprise conducting an amplification reaction. The amplification reaction may be selected from rolling circle amplification (RCA), hyperbranched RCA, RT-RCA, PCR and its variants, digital PCR, qPCR, and RT-qPCR. The methods may further comprise reverse transcribing (RT) the processed target polynucleotide before amplifying by PCR, wherein the processed target polynucleotide is RNA, to produce a processed polynucleotide cDNA. The processed polynucleotide cDNA may subsequently be amplified. RT-qPCR amplification of the circularized processed polynucleotide, wherein the processed target polynucleotide is RNA, may comprise miR-ID® as described by Kumar, P. et al. 2011. RNA 17: 365-380.

Amplifying may comprise ligating an adapter to the processed target polynucleotide. The adapter may comprise a tag, a barcode, a label, a primer annealing sequence, a cleavage site, or a hybridization site.

Detecting

The methods disclosed herein may comprise detecting the processed target polynucleotide. The methods disclosed herein may comprise detecting the amplified processed polynucleotide.

Detecting may be accomplished with a sequencing method. The sequencing method may comprise Sanger sequencing. The sequencing method may comprise next-generation sequencing. The sequencing method may comprise direct single-molecule sequencing.

Detecting the may comprise running a product of an amplification reaction on a gel. Detecting may comprise reading an output of a qPCR machine. Detecting may be performed in end-point or in real-time formats of these amplification reactions.

Detecting in real-time formats of these amplification reactions may comprise contacting the amplified processed polynucleotide with a single due. The single dye may be selected from SYBR Green, EvaGreen and SYTO dyes.

Detecting may comprise contacting the processed target polynucleotide or amplified processed polynucleotide with a probe. The probe may be a hybridization probe relying on fluorescence resonance energy transfer (FRET) for quantitation (FRET-probe). The FRET-probe may be selected from TaqMan probe, molecular beacon probe, Eclipse Probe and dual-hybridization probes.

Detecting may comprise contacting the processed target polynucleotide or amplified processed polynucleotide with a primer relying on fluorescence resonance energy transfer (FRET) for quantitation (FRET-primer). The FRET-primer may be selected from Amplifluor/UniPrimer, Scorpion PCR Primer, LUX PCR Primers and QZyme PCR Primers.

Target Polynucleotides/Samples

Disclosed herein are methods and compositions for detecting target polynucleotides. The methods may comprise detecting the target polynucleotide in a sample. Detecting the target polynucleotide in the sample may comprise isolating and/or purifying total RNA and/or DNA from the sample. Methods of isolating and/or purifying nucleic acids from samples are well known in the art. Alternatively, detecting the target polynucleotide in the sample may not require isolating and/or purifying nucleic acids from the sample. The target polynucleotide may be detected directly in the sample.

The target polynucleotide may be greater than about 10, about 15, about 20, about 30, about 40, about 50, about 100, about 150, about 200, about 250, about 300, about 500, about 1000, about 1500, about 2000, about 5000, or about 10,000 nucleotides in length.

The target polynucleotide may be a nucleic acid that has been fragmented, preserved, fixed, paraffin-embedded, stored, shipped, frozen, thawed, heated, and/or sheared. The nucleic acid may have been stored for days, months or years. The target polynucleotide may be obtained from or previously located in a formaldehyde fixed tissue.

The target polynucleotide may be an RNA molecule. The RNA molecule may be an mRNA molecule. The RNA molecule may be selected from a group consisting of: mRNA, viral RNA, viroid RNA, virusoid RNA, ribosomal RNA, tRNA, pre-tRNA, pre-mRNA, long non-coding RNA (lncRNA), snRNA, circular RNA (circRNA), pre-miRNA, pri-miRNA, vector-expressed RNA, RNA transcript, and synthetic RNA. In some instances, the RNA is not a miRNA molecule.

The target polynucleotide may be a DNA molecule. The DNA molecule may be selected from a group consisting of genomic DNA, viral DNA, mitochondrial DNA, plasmid DNA, amplified DNA, and synthetic DNA. The DNA may be eukaryotic DNA. The DNA may be prokaryotic DNA.

The portion of the target polynucleotide that is hybridized to the TSO may be between about 13 to about 100 nucleotides, between about 18 to about 60 nucleotides, or between about 20 to about 30 nucleotides.

The first TSO region may comprise at least one nucleotide. The first TSO region may comprise more than one nucleotide. The first TSO region may comprise more than one nucleotide. The first TSO region may comprise more than about 3, about 5, about 10, about 15, about 20, about 30, about 40, about 50, about 100, about 150, about 200, about 250, or about 300 nucleotides. The first TSO region may comprise less than about 1000 nucleotides.

The second TSO region may comprise at least three nucleotides. The second TSO region may comprise more than three nucleotides. The third TSO region may comprise more than about 3, about 5, about 10, about 15, about 20, about 30, about 40, about 50, about 100, about 150, about 200, about 250, or about 300 nucleotides. The second TSO region may comprise less than about 1000 nucleotides.

The third TSO region may comprise at least one nucleotide. The third TSO region may comprise more than one nucleotide. The third TSO region may comprise more than about 3, about 5, about 10, about 15, about 20, about 30, about 40, about 50, about 100, about 150, about 200, about 250, or about 300 nucleotides. The third TSO region may comprise less than about 1000 nucleotides.

The first TSO region may comprise at least five nucleotides. The second TSO region may comprise at least ten nucleotides. The third TSO region may comprise at least five nucleotides.

The portion of the target polynucleotide that is hybridized to the TSO may comprise 1, 2, or 3 or more nucleotide mismatches with the TSO. The mismatch may: (a) to direct site-specific cleavage in the first and/or third target polynucleotide regions; (b) prevent site-specific-cleavage of the second target polynucleotide region; (c) increase sequence specificity of hybridization for all target polynucleotide regions; and/or (d) adjust duplex stability between the TSO and target polynucleotide for all regions The portion of the target polynucleotide that is hybridized to the TSO may comprise 5, 4, 3, 2, or 1 or fewer single nucleotide mismatches with the TSO. The portion of the target polynucleotide that is hybridized to the TSO may be referred to as a duplex. The duplex formed between the portion of the target molecule and the second TSO region may comprise at least 1 nucleotide mismatch per every 8 nucleotides in the duplex. The duplex formed between the portion of the target molecule and the first TSO region may comprise 1, 2, or 3 or more single nucleotide mismatches. The duplex formed between the portion of the target molecule and the first TSO region may comprise 5, 4, 3, 2, or 1 or fewer single nucleotide mismatches. The duplex formed between the portion of the target molecule and the third TSO region may comprise 1, 2, or 3 or more single nucleotide mismatches. The duplex formed between the portion of the target molecule and the third TSO region may comprise 5, 4, 3, 2, or 1 or fewer single nucleotide mismatches.

The sample may be a biological sample. The sample may comprise an intact cell, a cell lysate, a tissue, a slice of tissue, a block of tissue, and combinations thereof. The sample may comprise a biological fluid (bio fluid or body fluid). The biological fluid may be selected from blood, plasma, serum, saliva, milk, urine, semen and other glandular fluids. The biological fluid may be a cell-free bio fluid. The cell-free bio fluid (e.g. tears, saliva, cerebrospinal fluid, etc.) may be a biological fluid with absent of cells, or wherein cells have been removed. The sample may be obtained from an animal. The sample may be obtained from a plant. The sample may comprise a prokaryotic cell and/or a eukaryotic cell. The sample may be obtained from a subject. The subject may be or may have been affected by a disease or condition. The disease or condition may be cancer. The sample may be a tumor sample or portion thereof. The sample may comprise a malignant cell.

The target polynucleotides may be detected directly in the cell lysate, serum or plasma samples without prior isolation and/or purification of the total RNA and/or DNA.

The samples may comprise partially degraded polynucleotides from formaldehyde-fixed paraffin-embedded (FFPE) tissue blocks, serum, plasma or other cell-free bio fluids. The sample may comprise partially degraded, fragmented, and/or modified polynucleotide molecules. The fragmentation of polynucleotide molecules comprises the cleavage of one or more phosphodiester bonds between nucleotides. The modification of polynucleotide molecules may comprise a formation of one or more reaction products selected from a list comprising: abasic sites, modifications of nucleoside residues, cross-linking between nucleotides, cross-linking of nucleotides with amino acids, peptides and proteins.

Kits

Further disclosed herein are kits for use in detecting one or more target polynucleotides. The kit may comprise one or more target-specific oligonucleotides (TSOs) disclosed herein and one or more of the following components: a hybridization buffer; a cleavage or processing buffer; an enrichment/wash buffer; a release buffer; a circularization buffer; a target polynucleotide-specific RT primer; and a target polynucleotide-specific amplification primer. The kit may comprise one or more target polynucleotide-specific amplification primers. The kit may comprise a pair of target polynucleotide-specific amplification primers.

The hybridization buffer may be used in the hybridization of the target polynucleotide and the TSO. The processing or cleavage buffer may be used in the processing/cleavage of the TSO-hybridized target polynucleotides. Cleavage of the target polynucleotides may produce fragments of the target polynucleotide that are not hybridized to the TSO. The enrichment/wash buffer may be used in the separation or enrichment of the processed polynucleotide or TSO-hybridized target polynucleotide from the fragments of the target polynucleotides that are not hybridized to the TSO, non-hybridized polynucleotides and/or polynucleotide fragments, non-hybridized TSOs, and other solutes. The release buffer may be used in the dissociation/release of the processed target polynucleotide from the TSO. The circularization buffer may be used in the circularization of released, processed polynucleotides. A single, release-and-circularization buffer may be used for both dissociation of the processed polynucleotides from the TSO and circularization of the processed polynucleotide. The one or more target-specific RT primers may be used to reverse transcribe the target polynucleotide. The one or more target polynucleotide-specific RT primers may be used in RT-RCA of the circularized polynucleotide fragments. The one or more target polynucleotide-specific amplification primers may be used to amplify the processed target polynucleotide. The polynucleotide-specific amplification primers may be used in the PCR amplification an RT-RCA reaction.

EXAMPLES

The following illustrative examples are representative of embodiments of the compositions, applications, and methods described herein and are not meant to be limiting in any way.

Example 1 mR-FQ Detection of Full-Length and Fragmented GAPDH mRNA

Figure 2:
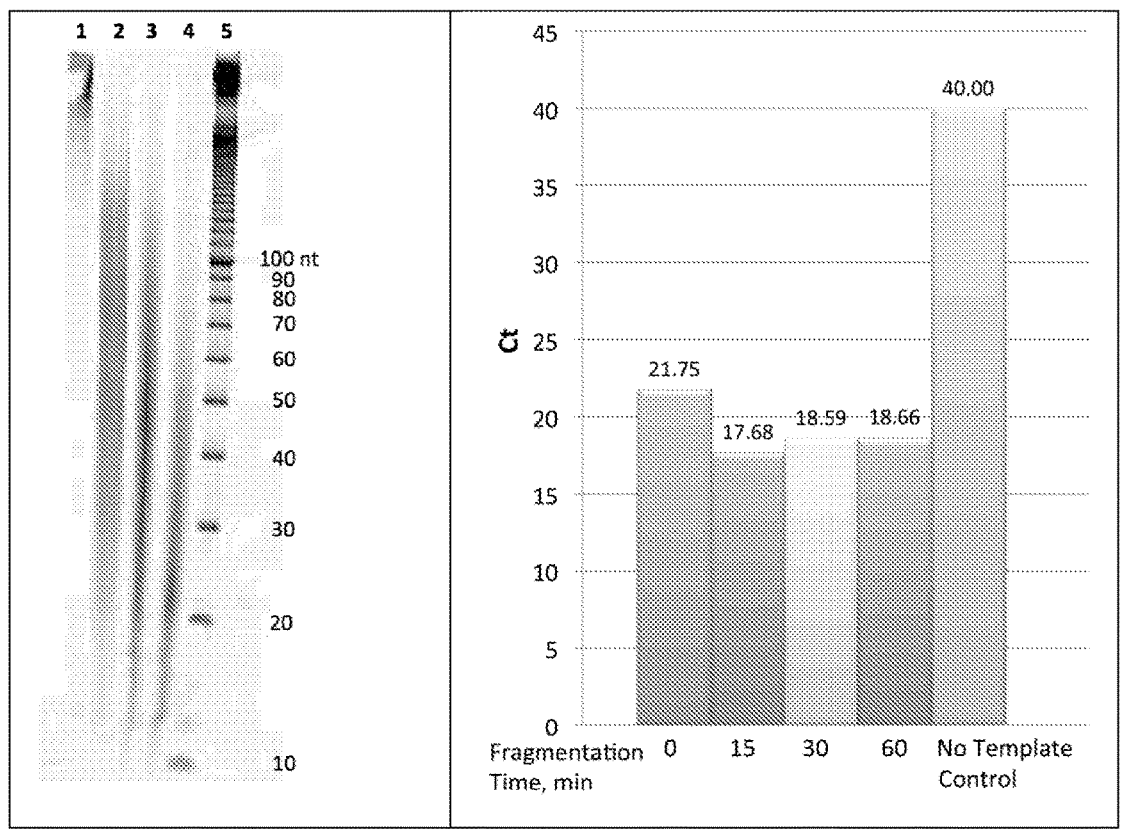
FIG. 2 shows the detection of an increasingly fragmented mRNA transcript by the mR-FQ method. The left panel of FIG. 2 shows an mRNA transcript (GAPDH, lane 1) with three increasing levels of transcript fragmentation induced by $ZnCl_2$ at elevated temperature (lanes 2 through 4). The right panel of FIG. 2 shows Ct values obtained using equal amounts of increasingly degraded mRNA fragments by mR-FQ and subsequent analysis by miR-ID®. The Ct values did not decrease with increasing fragmentation of the mRNA template.

GAPDH mRNA was transcribed from vector pCMV6-XL4/5/6 containing clone SC118869 (Origene). 20 μg aliquots of the RNA transcript were degraded for 0, 15, 30, or 60 min at 70° C. using an Ambion fragmentation kit (AM8740), following the kit instructions. FIG. 2 (left panel) shows an SDS gel of non-fragmented (lane 1) and fragmented RNA transcript (15, 30, 60 min in lanes 2, 3 and 4, respectively). The mR-FQ assay was conducted on the intact and fragmented samples as follows. Step 1: Hybridization of synthetic target mRNA with the target-specific oligonucleotide (TSO). 1 pM of a synthetic GAPDH mRNA fragment, GCUCAUUUCCUGGUAUGACAACG (SEQ ID NO: 1), was hybridized to 160 nM gccaattCGUUGUUAUACCAG UAAAUGAGCttgacaaa-3BioTEG (TSO, SEQ ID NO: 2) [wherein lower case is DNA; upper case is 2'-OMe RNA nucleotides; underlined nucleotides represent mismatches to the target sequence; and 3BioTEG is 3'-Biotin-TEG residue (IDT) that has an extended spacer arm.] in 10 μl of 1× RNase H buffer (NEB). The hybridization was conducted as follows: 80° C. for 2 min, cool to 40° C. at a 0.1° C./sec rate, 40° C. for 60 min, cool to 4° C. at a 0.1° C./sec rate. Step 2: RNase H digestion of target mRNA hybridized with TSO. 2.5 U RNAse H (NEB) were added to each sample after Step 1 and incubated at 37° C. for 1 hour. The RNA-TSO duplexes were captured by incubation with 20 μg streptavidin-coated magnetic beads (NEB) in 400 μl NEB buffer 3 at room temperature for 15 min. The beads were separated on a magnetic rack (NEB) and washed three times with 500 μl wash buffer (100 mM NaCl, 1 mM EDTA, 20 mM Tris-HCl, pH 7.5). The captured RNA fragments were released from the beads and circularized by adding 10 μl release buffer (66 mM K-acetate, 0.5 mM DTT, 5 mM $MgCl_2$, 1M betaine, 33 mM Tris-acetate, pH 7.5) containing 100 U CircLigase II (Epicentre) and incubated at 60° C. for 15 min. Following the ligation reaction, the beads were separated on a magnetic rack and the circularized RNA in solution was used for miR-ID® assays essentially as described in (Kumar, P. et al. 2011. RNA 17: 365-380), using a GAPDH-specific RT primer, GTCATACCAG (SEQ ID NO: 3) and a pair of PCR primers: forward PCR primer, CATTTCCTGGTAT-GACAACG (SEQ ID NO: 4), and reverse PCR primer, TGTCATACCAGGAAATGAGC (SEQ ID NO: 5). The right panel of FIG. 2 shows Ct values obtained using equal amounts of increasingly degraded mRNA fragments by mR-FQ and subsequent analysis by miR-ID®. The Ct values are improving with some fragmentation and are not changing significantly with increasing fragmentation.

Example 2

Increase of mR-FQ Sensitivity by Using Mismatches Between TSO and Target mRNA

Figure 3:
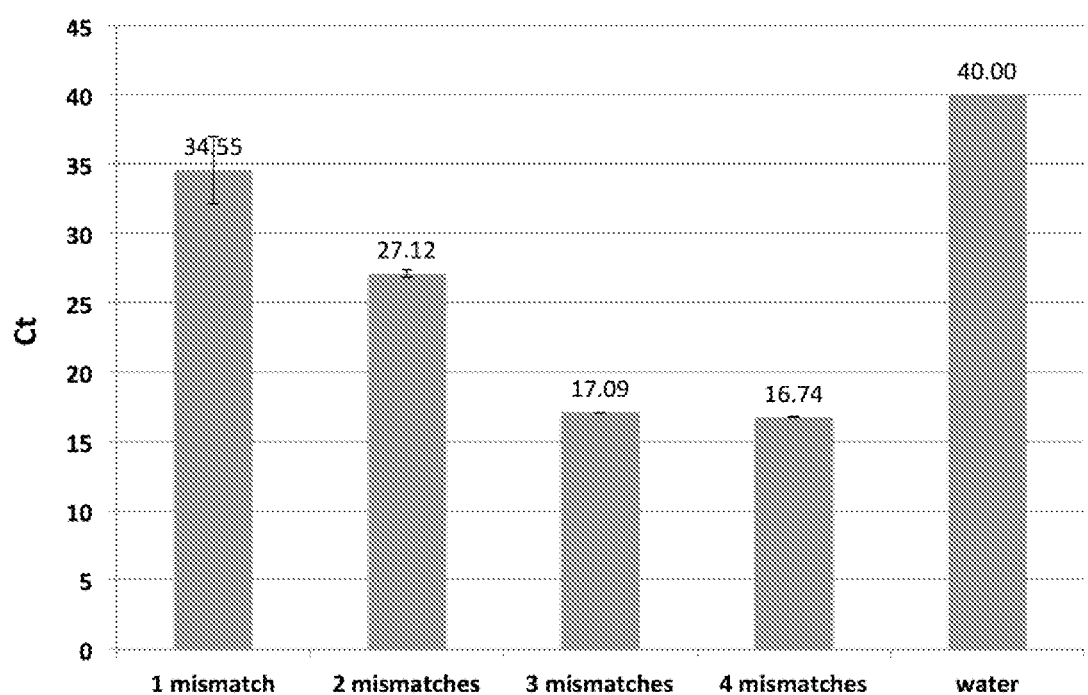
FIG. 3 shows an example of mR-FQ analysis using TSOs with 1, 2, 3, or 4 mismatches, with best detection in this experiment with TSOs having 3 or 4 mismatches.

For the target capture step in the mR-FQ procedure, the following synthetic TSOs containing respectively 1, 2, 3, or 4 mismatches (underlined nucleotides) were used with the target sequence (see below): (1) tctcgctcCUGGAAGAUG AUGAUGGGAUUUCcattgatg/3BioTEG (SEQ ID NO: 6), (2) tctcgctcCUGGAAUAUG AUGAUGGGAUUUCcattgatg/3BioTEG (SEQ ID NO: 7), (3) tctcgctcCUGGAAUAUGAUGAUG GGAUUUCcattgatg/3BioTEG (SEQ ID NO: 8), and (4) tctcgctcCUGGAAUAUGAUAAUG GGAUUUCcattgatg/3BioTEG (SEQ ID NO: 9), wherein lower case is DNA; upper case is 2'-OMe RNA nucleotides; and 3BioTEG is 3'-Biotin-TEG residue (IDT). The mR-FQ assays with these TSOs were conducted essentially as described in Example 1, except that the following primers were used: RT primer, GGTGATGGGA (SEQ ID NO: 10), forward PCR primer, ATCCCATCACCATCTTCCAG (SEQ ID NO: 11) and reverse PCR primer, GAAGATGGT-GATGGGATTTC (SEQ ID NO: 12). The experiment was conducted with synthetic target RNA, GAAATCCCAT-CACCATCTTCCAG (SEQ ID NO: 13). All synthetic oligonucleotides were from IDT. The optimal detection was achieved with TSOs that had three or four mismatches to the target sequence (as shown in FIG. 3).

Example 3

Figure 4:
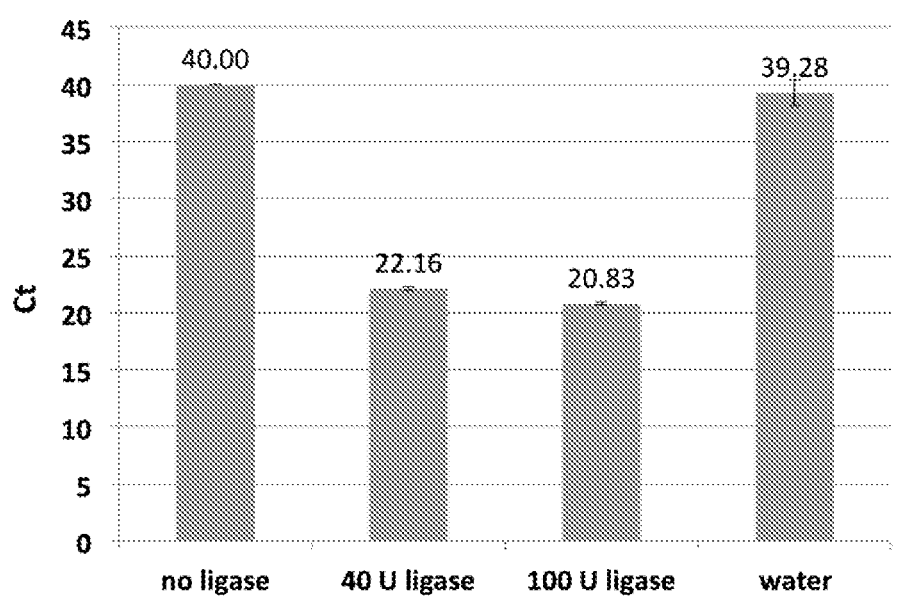
FIG. 4 shows quantification of GAPDH mRNA by mR-FQ using 0, 40, or 100 U CircLigase. The data demonstrate that circularization of the captured and excised template is essential for the target mRNA quantification by mR-FQ since without circularization the target mRNA is not detectable (Ct is at background level).

Circularization of Captured and Excised mRNA Fragments is Required for Efficient mRNA Quantification Steps 1 and 2 of the mR-FQ assay were essentially performed as described in Example 1, except that that the ligation reaction was performed with 0, 40, or 100 U CircLigase II (Epicentre) in 10 μL-reactions. Use of 100 U of CircLigase II provides slightly higher assay sensitivity than use of 40 U, whereas the target mRNA is not detectable (Ct is at background level) without CircLigase II treatment. The data shown in FIG. 4 demonstrate that circularization of the captured and excised template is essential for the target mRNA quantification by mR-FQ.

Example 4 mR-FQ Assays have Higher Sensitivity and Better Reproducibility than TaqMan RT-qPCR Assays in Detection of Highly Degraded mRNAs from FFPE Samples

Figure 5A:
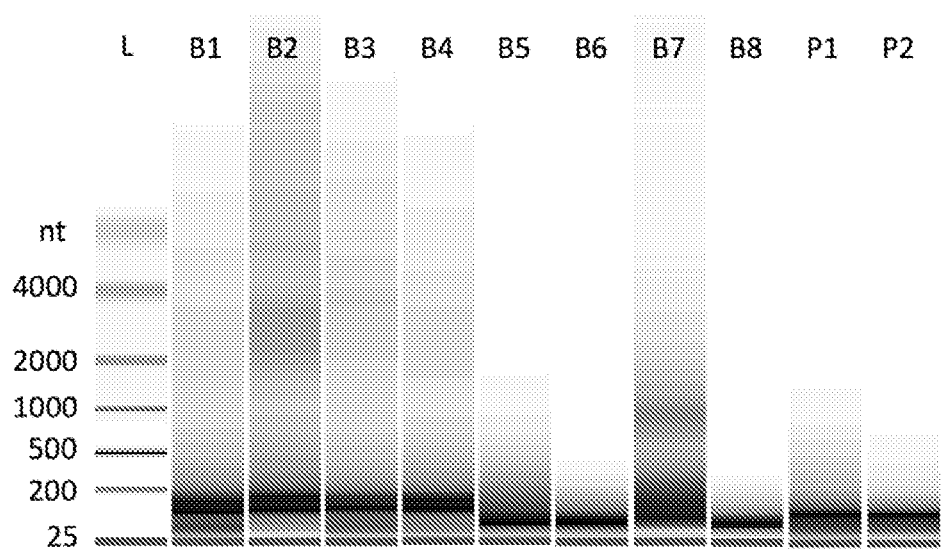
FIG. 5A-C shows quantification of highly degraded HER-2 and GAPDH mRNAs isolated from FFPE samples using TaqMan RT-qPCR or mR-FQ assays.
Figures 5B, 5C:
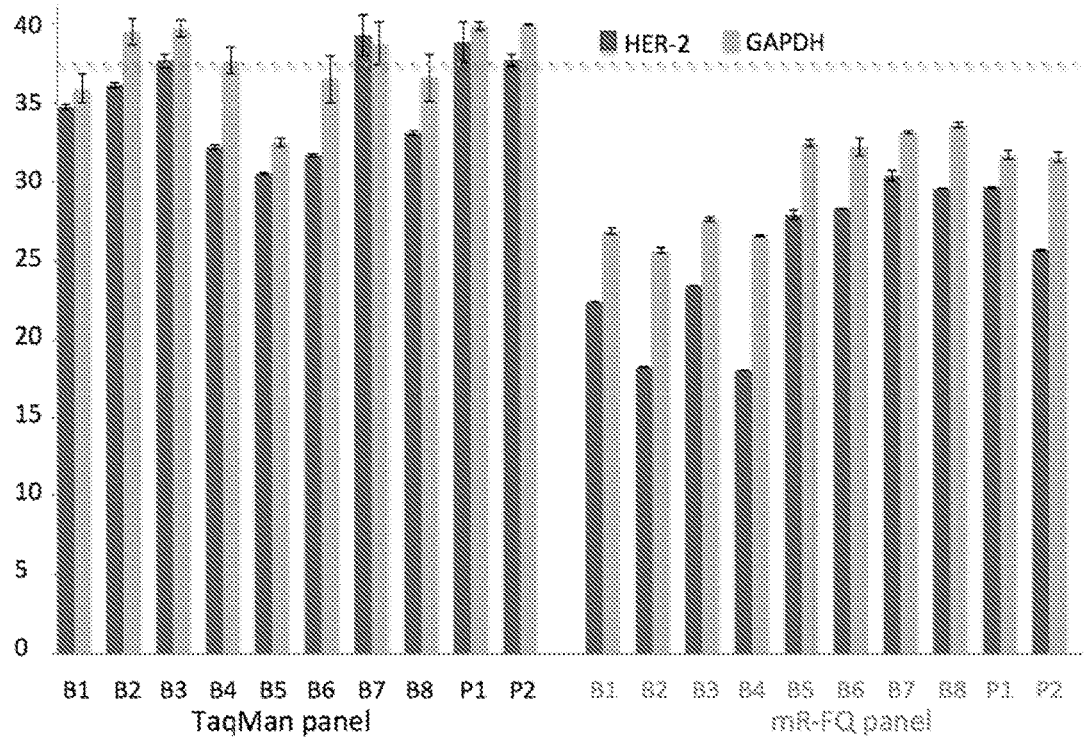

Total RNA was isolated from ten FFPE tissue samples (2 mm thick, ~0.25 cm² tissue area) using the RecoverAll™ Total Nucleic Acid Isolation Kit (Ambion/Life Technologies). These included four 6-year-old (B1-B4) and four 12-year-old (B5-B8) breast cancer samples as well as two 15-year-old prostate cancer samples (P1-P2, all from BioServe). Agilent Bioanalyzer traces indicate significant RNA degradation levels in all samples (FIG. 5A). FIG. 5B shows the quantification of HER-2 and GAPDH mRNAs in 500 ng of total RNAs isolated from these FFPE samples by TaqMan (left panel) and mR-FQ assays (right panel). The mR-FQ assays were performed as described in Example 1 including sequences of GAPDH-specific primers and TSOs. The HER-2-specific primers and TSOs were as follows: RT primer, GTATGCTTCG (SEQ ID NO: 14), forward PCR primer, AATCTTAGACGAAGCATACG (SEQ ID NO: 15), reverse PCR primer ATGCTTCGTCTAAGATTTCT (SEQ ID NO: 16); and TSO agccatcaCGUAUACUUC AUCUAAUAUUUCUttgttggc/3BioTEG (SEQ ID NO: 17), wherein lower case is DNA, upper case is 2'-OMe RNA nucleotides, and underlined nucleotides: mismatches to the selected target RNA sequence, AGAAAUCUUAGAC-GAAGCAUACG (SEQ ID NO: 18). All synthetic oligonucleotides were from IDT (3BioTEG is 3'-Biotin-TEG residue). For the TaqMan assays, the RT reactions were performed using MultiScribe™ Reverse transcriptase (Life Technologies) with random RT primers according to the Life Technologies protocol. For the qPCR quantitation of GAPDH, TaqMan assay Hs99999905_m1 (PCR amplicon length, 124 bp) was used. For the TaqMan HER-2 analysis, we used assay Hs01001580_m1 (PCR amplicon length, 60 bp). Both target-specific assays were used in combination with the TaqMan Universal Master Mix (Life Technologies). All qPCR steps were performed in triplicate and the resulting average Ct values (±standard deviation) are shown in FIG. 5B. The red cut-off line is placed at a Ct value of 37, above which data become unreliable. The non-template controls for both methods showed background levels of Ct~40 (data not shown). Overall Ct values were higher for TaqMan assays (left panel) than for mR-FQ assays (right panel). The data indicate that mR-FQ assays (right panel) have significantly higher sensitivity (lower Ct values) and better reproducibility (smaller error bars) than TaqMan assays (left panel). FIG. 5C shows the calculated delta-delta Ct values, which are typically used to compare transcription levels in relation to a reference gene among different samples. The analyzed breast-cancer samples B2 and B4 have been classified as HER-2 positive by immuno-cytology (BioServe), whereas samples B1 and B3 are classified at HER-2 negative. The delta-delta Ct values calculated from mR-FQ measurements confirm a higher HER-2/GAPDH ratio in HER-2 positive samples in comparison to the ratio from the HER-2 negative sample B1, validating mR-FQ as a reliable method to measure expression of these genes.

Figure 6:
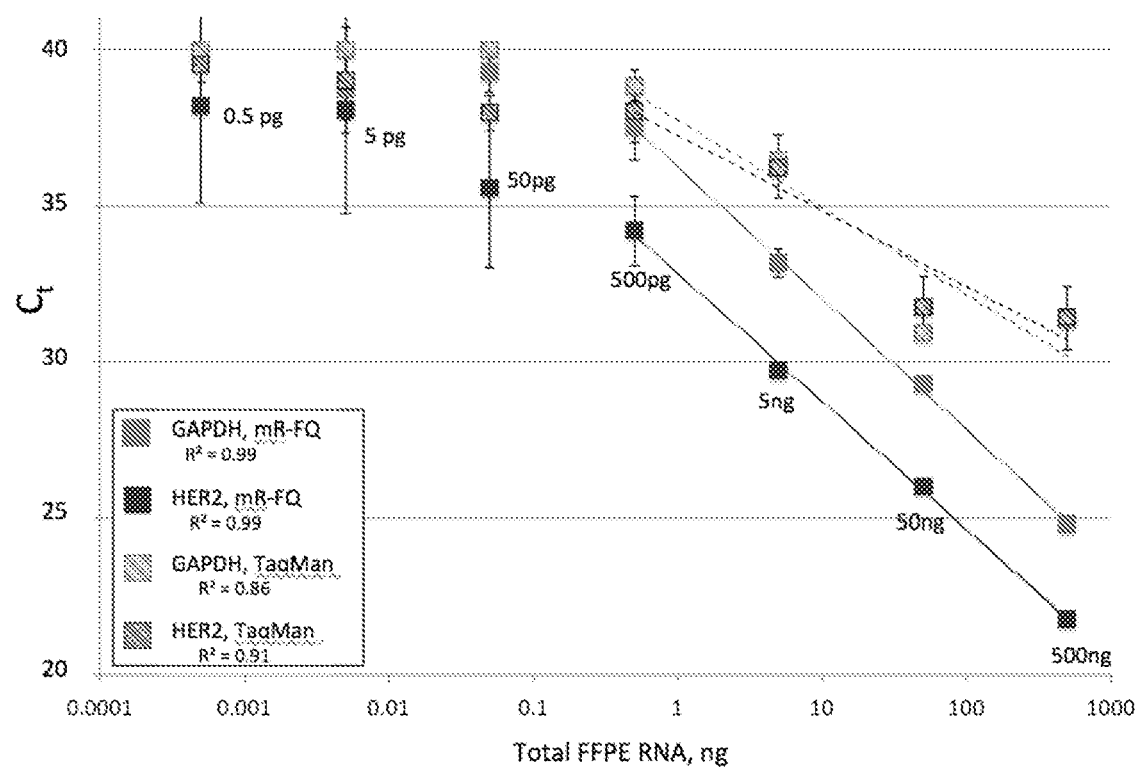
FIG. 6 shows a standard dilution plot for inputs of total RNA isolated from FFPE breast cancer samples (from FIG. 5A) for detection of endogenous HER-2 and GAPDH mRNAs by mR-FQ and TaqMan RT-qPCR assays. The mR-FQ assay outperforms TaqMan assays in sensitivity and can reliably quantify HER-2 and GAPDH mRNAs using 500 pg or more total RNA from FFPE samples.

Example 5 mR-FQ has Better Detection Limit and Higher Reproducibility than TaqMan in Detection of GAPDH and HER-2 mRNAs from FFPE Samples mR-FQ and TaqMan assays were conducted as described in Example 4. FIG. 6 shows a plot for standard dilution experiments performed for various amounts of total RNA isolated from FFPE breast cancer samples for detection of HER-2 and GAPDH mRNAs by both methods. The mR-FQ method (filled squares) reliably quantified HER-2 (darker squares) and GAPDH (lighter squares) mRNA using 500 pg or more total RNA from FFPE samples. The TaqMan method (striped squares) suffered from some qPCR inhibition in the high RNA input sample (500 ng) and showed generally higher Ct values per comparable total RNA input. At a total RNA input of 50 pg or less, both methods returned unreliable Ct values.

The invention claimed is:

1. A method for detecting a target polynucleotide having a length of about 10 to about 250 nucleotides, comprising:
   a. hybridizing the target polynucleotide with a target specific oligonucleotide (TSO) to produce a TSO-hybridized target polynucleotide, wherein the TSO comprises:
      i. a first TSO region that hybridizes to a first target polynucleotide region;
      ii. a second TSO region that hybridizes to a second target polynucleotide region; and
      iii. a third TSO region that hybridizes to a third target polynucleotide region; wherein the second TSO region connects the first and third TSO regions; and wherein upon hybridization of the TSO to the target polynucleotide, the first and third of target polynucleotide regions become substrates for cleavage by a cleaving agent, and the second target polynucleotide region is not a substrate for cleavage by the cleaving agent;
   b. cleaving the target polynucleotide at a first site within the first target polynucleotide region and a second site within the third target polynucleotide region to generate a TSO-hybridized processed target polynucleotide,
   c. amplifying the TSO-hybridized processed target polynucleotide to produce an amplified processed polynucleotide, wherein amplifying the TSO-hybridized processed target polynucleotide comprises circularizing the processed target polynucleotide to produce a circular processed target polynucleotide and amplifying the circular processed target polynucleotide: and
   d. detecting the amplified processed polynucleotide, thereby detecting the target polynucleotide.

2. The method of claim 1, further comprising purifying or isolating the TSO-hybridized processed polynucleotide by:
   a. capturing the TSO-hybridized processed polynucleotide to produce a captured TSO-hybridized processed polynucleotide; and
   b. separating the captured TSO-hybridized processed polynucleotide from other polynucleotides or their fragments and other solutes that are not hybridized to the TSO.

3. The method of claim 2, wherein the TSO comprises a capture moiety and wherein capturing the TSO-hybridized processed polynucleotide comprises capturing the capture moiety with a binding moiety.

4. The method of claim 1, further comprising releasing the TSO-hybridized processed target polynucleotide from hybridization with the TSO before amplifying.

5. The method of claim 1, wherein circularizing occurs with at least partial dissociation of the TSO-hybridized processed target polynucleotide from the TSO.

6. The method of claim 1, wherein the circularizing comprises contacting the TSO-hybridized processed target polynucleotide with a ligase.

7. The method of claim 6, wherein the ligase is a thermostable ligase.

8. The method of claim 1, wherein the detecting comprises sequencing the amplified processed polynucleotide.

9. The method of claim 1, wherein the detecting comprises an amplification method selected from a group consisting of: rolling circle amplification (RCA), hyperbranched RCA, RT-RCA, PCR and its variants, digital PCR, qPCR, and RT-qPCR.

10. The method of claim 1, wherein the target polynucleotide is RNA or DNA.

11. The method of claim 1, wherein the TSO-hybridized processed target polynucleotide is in the range of 18 to 60 nucleotides.

12. The method of claim 1, wherein the second TSO region possesses a sequence that contains one or more mismatches with a sequence of the second target polynucleotide region.

13. The method of claim 1, wherein the first and third TSO regions consist essentially of DNA residues and the second TSO region consists essentially of unmodified and/or chemically modified RNA residues.

14. The method of claim 1, wherein the cleaving is accomplished by ribonuclease H or an analog thereof.

15. The method of claim 12, wherein the cleaving of the TSO-hybridized polynucleotide is performed by a duplex-specific nuclease.

16. The method of claim 1, wherein the first and/or third TSO regions further comprise a catalytic nucleic acid moiety that cleaves the target polynucleotide after hybridization with the TSO, wherein the catalytic nucleic acid moiety is located in a region of the first and/or third TSO regions that is not complementary to the target polynucleotide.

17. The method of claim 3, wherein the capture moiety is selected from the group consisting of: a hapten, a ligand, a metal-chelating moiety, a nanoparticle, and an oligonucleotide linker.

18. The method of claim 3, wherein the binding moiety is located on a solid support.

19. The method of claim 1, wherein the TSO is attached to a solid support.

20. The method of claim 1, wherein the target polynucleotide is present in a sample selected from the group consisting of: a sample that contains partially degraded polynucleotides; a formaldehyde-fixed paraffin-embedded (FFPE) tissue block; a cell lysate; a serum sample; a plasma sample; and a cell-free bio fluid.

21. The method of claim 20, wherein the target polynucleotide is detected directly in the sample without prior isolation and/or purification of total nucleic acids from the sample.

* * * * *